United States Patent [19]

Richards et al.

[11] Patent Number: 4,581,331

[45] Date of Patent: Apr. 8, 1986

[54] METHOD FOR THE RAPID DETECTION OF VIRUS AND VIRAL ANTIGENS

[75] Inventors: James C. Richards, Wilmington, Del.; Dennis L. Murray, Williamston, Mich.

[73] Assignee: E. I. Du Pont de Nemours and Company, Wilmington, Del.; Board of Trustees, East Lansing, Mich.

[21] Appl. No.: 537,320

[22] Filed: Sep. 29, 1983

[51] Int. Cl.$^4$ .......................... C12Q 1/00; C12Q 1/70; C12Q 1/68; G01N 33/53

[52] U.S. Cl. ........................................... 435/4; 435/5; 435/6; 435/7; 435/29; 435/30; 436/825; 935/78

[58] Field of Search .......................... 424/9; 435/4-7, 435/29, 30; 935/78; 436/825

[56] References Cited

U.S. PATENT DOCUMENTS

| | | | |
|---|---|---|---|
| 3,875,012 | 4/1975 | Dorn et al. | 435/30 |
| 3,883,425 | 5/1975 | Dorn | 435/2 |
| 3,928,139 | 12/1975 | Dorn | 435/30 |
| 3,932,222 | 1/1976 | Dorn | 435/34 |
| 3,935,066 | 1/1976 | Apostolov | 435/240 |
| 4,131,512 | 12/1978 | Dorn | 435/30 |
| 4,212,948 | 7/1980 | Dorn | 435/34 |
| 4,358,535 | 11/1982 | Falkow et al. | 435/5 |
| 4,497,900 | 2/1985 | Abram et al. | 436/825 |

FOREIGN PATENT DOCUMENTS

| | | | |
|---|---|---|---|
| 97633 | 1/1984 | European Pat. Off. | 435/5 |
| 416959 | 2/1981 | Sweden | 435/30 |

OTHER PUBLICATIONS

Emini et al, J. Virol., 43 (1982) 997–1005.

Primary Examiner—Christine M. Nucker
Attorney, Agent, or Firm—Gerald E. Deitch

[57] ABSTRACT

A method for the rapid detection of virus and viral antigens associated with somatic cells in biological test samples is disclosed. The method comprises lysing the cells with a lytic agent to reveal virus or viral antigens for participation in a virus detection system. The lytic agent is chosen for its biological neutrality in the detection system, particularly its inability to produce a cytopathic effect in tissue culture.

8 Claims, No Drawings

METHOD FOR THE RAPID DETECTION OF VIRUS AND VIRAL ANTIGENS

TECHNICAL FIELD

This invention relates to a novel method for processing samples of biological origin and conducting rapid, substantially interference-free diagnosis of the presence of virus and viral antigens.

BACKGROUND OF THE INVENTION

Reliable determination of viral infection through analysis of biological specimens for infectious virus and viral antigens is important because subsequent medical treatment depends upon the ability to differentiate between infections caused by bacteria or viruses. The selection of appropriate medical treatment is predicated on correct diagnosis of etiologic agent(s) and the ability to determine the group to which said agent(s) belongs.

The rapid diagnosis of bacterial infection by analysis of biological specimens, preferably peripheral blood samples, through the process of lysis centrifugation is described in detail in U.S. Pat. Nos. 3,875,012, 3,928,139, 3,932,222, 4,131,512, and 4,212,948 which are incorporated herein by reference. The apparatus disclosed and methods applied provide a means to concentrate microbial pathogens from a large sample volume to a reduced sample volume by selective lysis of somatic cells which leaves microbial pathogen cells intact which sediment into a concentrated zone upon application of centrifugal forces. Microbial pathogens concentrated into the zone are detected through growth on enrichment media which promote cell replication and expression of specific characteristics which aid in microbial species identification.

Previous methods commonly employed for recovering infectious virus from samples of biological origin, specifically peripheral blood specimens, include contacting samples of anticoagulant-treated whole blood or whole blood processed to serum with indicator cells specifically susceptible to viral cytopathic effects. Viable virus particles contained in the blood or serum sample infect susceptible indicator cells over a typical period of from 12 to 38 days under favorable incubation conditions. Infected cells undergo virus-induced lysis which appears as a clear area on confluent host cell layers. The relative degree of viral infectivity in the sample is determined by quantitating the clear areas, which constitute the viral cytopathic effect (CPE). Direct placement of whole anticoagulated blood has, as a major disadvantage, presence of erythrocytes in vast excess over other cells, e.g., polymorphonuclear leukocytes (PMN), monocytes, and lymphocytes which are more likely to contain virus. As a result, erythrocytes interfere with intimate contact between PMN, monocyte or lymphocyte cells and indicator tissue culture cells and thereby block efficient passage of virus from somatic cells to indicator tissue culture cells. Use of coagulated blood, namely, the serum fraction, results in loss of somatic cells (e.g., PMN, monocytes, and lymphocytes) which contain virus, and therefore also results in loss of virus contained in the somatic cells.

A significant improvement in the application of whole blood or blood serum samples to determine viral infectivity consists of obtaining through centrifugation an enriched specimen of white blood cells composed particularly of leukocytes which are known to phagocytize or engulf virus particles. One process provides a "buffy coat" or mixed leukocyte cell layer from an anticoagulant-treated whole blood specimen. The mixed leukocyte cell population sediments slower than the erythrocyte cell population upon centrifugation and therefore can be found layered above erythrocytes. This layer of mixed leukocytes can be carefully removed by pipette aspiration and contacted with a susceptible cell population for detection of virus by cytopathic effect. A further improvement for processing biological specimens is the use of materials which create density gradients upon centrifugation such as Ficoll-Paque/Dextran as in the method of Howell, C. L. et al., Journal of Clinical Microbiology 1979, 10(4):533–537. The mixed leukocyte cell population is further separated in this process into lymphocyte, monocyte, and PMN sub-populations. It is well known that certain viruses such as, but not limited to, Cytomegalovirus, are preferentially associated with the PMN population, while others, such as, but not limited to, Adenovirus and Varicella, are more often associated with monocyte populations. The selective isolation of these populations during centrifugation offers an improvement over conventional centrifugation by enriching the quantity of virus-bearing cells recovered from fractionation of a peripheral blood specimen. Detection of virus by contacting aliquots of each enriched leukocyte fraction with susceptible cell systems and quantitating cytopathic effect has been improved by increasing the number, variety, and frequency of recovered virus. However, the major disadvantage of both the "buffy coat" and density gradient centrifugation techniques is that several laborious, time-consuming steps are required with a relatively high level of technical skill to obtain suitable specimens. Unfortunately, the improved diagnostic capability realized with leukocyte population fractionation requires this level of effort. There is a need for a rapid method to detect virus or viral antigens in biological samples which does not require sophisticated, multi-step procedures to obtain suitable analytical specimens for virus detection systems, particularly tissue culture.

SUMMARY OF THE INVENTION

This need is met in substantial measure by the present invention which is a method for the rapid detection and determination of virus or viral antigens suspected of being contained in somatic cells in a test sample, comprising: (i) forming a reaction mixture by contacting the test sample with a solution having contained therein a lytic agent capable of lysing the somatic cells to release virus or viral antigens contained therein or thereon: (ii) separating the reaction mixture into a first fraction containing virus and viral antigens and the lytic agent and a second fraction substantially free of virus or viral antigens: (iii) contacting an aliquot of the first fraction with a virus detection system capable of exhibiting an effect attributable to the presence of the virus or viral antigens in the first fraction, but which is not attributable to the lytic agent.

DETAILED DESCRIPTION OF THE INVENTION

The present invention provides a rapid means for recovering from somatic cells in biological samples virus or viral antigens contained therein or thereon whose availability for participation in various detection systems might be otherwise blocked. The sample, generally whole blood, is mixed with a solution, generally aqueous such as isotonic saline, containing a lytic agent which is capable of lysing the somatic cells to reveal virus or viral antigens, but which is incapable of interfering with viral detection systems, in particular, producing false positive CPE in tissue culture. The lytic agent should be used at the minimum concentration required for lysis of the somatic cells.

After mixing the sample with the solution containing the lytic agent, the reaction mixture so formed is separated, preferably by centrifugation, into two fractions, a first fraction, which in the case of centrifugation is the supernatant fluid which contains the released virus and/or viral antigens, and a second fraction containing cellular debris and other material having a sedimentation rate greater than the virus or viral antigens, e.g. bacteria. A highly preferred device for performing both the lysis and separation is the tube described in U.S. Pat. No. 4,212,948 issued to Dorn on July 15, 1980 and incorporated herein by reference. Highly preferred lytic agents are sapogenin glycosides. See Mc Ilroy, *The Plant Glycosides*, Edward Arnold & Co., London 1951. A particularly preferred lytic agent is the detoxified saponin described in U.S. Pat. No. 3,883,425, issued to Dorn on May 13, 1975 and incorporated herein by reference. Both these lytic agents are capable of lysing somatic cells contained in the sample, but are not cytopathic in many tissue culture systems, e.g., Hep 2, HeLa, MDCK, and MDBK. The table below lists several viruses which can be detected rapidly using the present invention and the corresponding tissue culture systems into which they can be introduced to produce CPE which is not attributable to the lytic agent.

TABLE

| Virus | Cell Line |
|---|---|
| Adenovirus | Hep 2 |
| Coxsackie B5 | HeLa |
| Influenza A (strain PR8-34) | MDCK |
| Vesicular Stomatitis Virus | MDBK |

Other separation means will be readily apparent to those skilled in the art and include ultra-filtration, microporous filtration (0.22μ pore diameter filter such as those available from Millipore Co.), gel filtration, and dialysis.

Centrifugation, because of ease and simplicty is preferred. Generally, centrifugal forces of about 1000 to 10,000×g, preferably 3000×g will be used. An aliquot of the supernatant fluid is aspirated and applied directly to well known virus indicator systems which can include tissue culture, immunoassay, nucleic acid hybridization, electron microscopy, live animals, etc. An advantage of the present invention resides in the ability to increase the amount of detectable virus or viral antigens through lysis and thereby increase the sensitivity of the detection systems recited above. The principal advantage becomes manifest in the use of tissue culture systems. The lytic agents recited above, i.e. the sapogenin glycosides, while capable of lysing somatic cells, do not, unlike virtually every other lytic agent used in virology (e.g. ionic and non-ionic detergents) produce a CPE in tissue culture, thereby allowing the first fraction of the separation to be inoculated directly into tissue culture. Any CPE subsequently observed will be attributable to the presence of the virus and not the presence of the lytic agent.

What is claimed is:

1. A method for the rapid detection and determination of virus or viral antigens suspected of being contained in somatic cells in a test sample, comprising: (i) forming a reaction mixture by contacting the test sample with a solution having contained therein a sapogenin glycoside capable of lysing the somatic cells to release virus or viral antigens contained therein or thereon: (ii) separating the reaction mixture into a first fraction containing virus and viral antigens and the sapogenin glycoside and a second fraction substantially free of virus or viral antigens: (iii) contacting an aliquot of the first fraction with a virus detection system capable of exhibiting an effect attributable to the presence of the virus or viral antigens in the first fraction, but which is not attributable to the sapogenin glycoside.

2. The method of claim 1 wherein the sapogenin glycoside is detoxified saponin.

3. The method of claim 1 wherein the separating step comprises centrifugation.

4. The method of claim 3 wherein the centrifugation is carried out at about 3000×g.

5. The method of claim 1 wherein the detection system comprises tissue culture susceptible to infection by the virus.

6. The method of claim 1 wherein the detection system comprises immunoassay.

7. The method of claim 1 wherein the detection system comprises nucleic acid hybridization.

8. The method of claim 1 wherein the detection system comprises live animals susceptible to infection by the virus.

* * * * *